US009675529B2

(12) United States Patent
Abuelyaman et al.

(10) Patent No.: US 9,675,529 B2
(45) Date of Patent: Jun. 13, 2017

(54) DENTAL COMPOSITION CONTAINING HIGH REFRACTIVE INDEX MONOMERS

(71) Applicant: 3M INNOVATIVE PROPERTIES COMPANY, St. Paul, MN (US)

(72) Inventors: Ahmed S. Abuelyaman, Woodbury, MN (US); Ann R. Fornof, St. Paul, MN (US); Larry R. Krepski, White Bear Lake, MN (US); William H. Moser, Edina, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 6 days.

(21) Appl. No.: 14/770,103

(22) PCT Filed: Apr. 8, 2014

(86) PCT No.: PCT/US2014/033254
§ 371 (c)(1),
(2) Date: Aug. 25, 2015

(87) PCT Pub. No.: WO2014/172138
PCT Pub. Date: Oct. 23, 2014

(65) Prior Publication Data
US 2016/0081887 A1    Mar. 24, 2016

Related U.S. Application Data

(60) Provisional application No. 61/811,852, filed on Apr. 15, 2013, provisional application No. 61/811,850, filed on Apr. 15, 2013.

(51) Int. Cl.
*A61K 6/083* (2006.01)
*A61C 5/00* (2017.01)
*A61C 13/15* (2006.01)
*A61K 6/00* (2006.01)

(52) U.S. Cl.
CPC ............... *A61K 6/083* (2013.01); *A61C 5/00* (2013.01); *A61C 19/003* (2013.01); *A61K 6/0005* (2013.01); *A61K 6/0023* (2013.01); *A61K 6/0073* (2013.01); *A61K 6/0835* (2013.01); *A61K 6/0047* (2013.01)

(58) Field of Classification Search
CPC ..... A61K 6/083; A61K 6/0005; A61K 6/0047
See application file for complete search history.

(56) References Cited

U.S. PATENT DOCUMENTS

| | | |
|---|---|---|
| 4,503,169 A | 3/1985 | Randklev |
| 4,540,723 A | 9/1985 | Ying |
| 5,130,347 A | 7/1992 | Mitra |
| 5,154,762 A | 10/1992 | Mitra |
| 5,501,727 A | 3/1996 | Wang |
| 5,506,279 A | 4/1996 | Babu |
| 5,545,676 A | 8/1996 | Palazzotto |
| 5,780,668 A | 7/1998 | Rheinberger |
| 5,925,715 A | 7/1999 | Mitra |
| 5,962,550 A | 10/1999 | Akahane |
| 6,126,922 A | 10/2000 | Rozzi |
| 6,387,981 B1 | 5/2002 | Zhang |
| 6,572,693 B1 | 6/2003 | Wu |
| 6,730,156 B1 | 5/2004 | Windisch |
| 6,794,520 B1 | 9/2004 | Moszner |
| 6,899,948 B2 | 5/2005 | Zhang |
| 7,090,721 B2 | 8/2006 | Craig |
| 7,090,722 B2 | 8/2006 | Budd |
| 7,156,911 B2 | 1/2007 | Kangas |
| 7,241,437 B2 | 7/2007 | Davidson |
| 7,393,882 B2 | 7/2008 | Wu |
| 7,449,499 B2 | 11/2008 | Craig |
| 7,452,924 B2 | 11/2008 | Aasen |
| 7,649,029 B2 | 1/2010 | Kolb |
| 7,838,110 B2 | 11/2010 | Zhu |
| 7,888,400 B2 | 2/2011 | Abuelyaman |
| 2008/0200582 A1* | 8/2008 | Craciun ........... B29D 11/00442 522/166 |
| 2009/0011388 A1 | 1/2009 | Craig |
| 2009/0018234 A1 | 1/2009 | Tokui |
| 2009/0298966 A1 | 12/2009 | Vanini |
| 2010/0004416 A1 | 1/2010 | Neffgen |
| 2010/0021869 A1 | 1/2010 | Abuelyaman |
| 2012/0050718 A1 | 3/2012 | Dazzi |
| 2012/0208965 A1* | 8/2012 | Joly ...................... C07C 69/593 525/386 |
| 2013/0012614 A1 | 1/2013 | Abuelyaman |

FOREIGN PATENT DOCUMENTS

| | | |
|---|---|---|
| DE | 102006045628 | 4/2008 |
| EP | 0684222 | 11/1995 |
| EP | 0710475 | 5/1996 |
| EP | 2401998 | 1/2012 |
| WO | WO 2008-082881 | 7/2008 |
| WO | WO 2010-027676 | 3/2010 |
| WO | WO 2010-048067 | 4/2010 |
| WO | WO 2012-112321 | 8/2012 |
| WO | WO 2014-074373 | 5/2014 |
| WO | WO 2014-099317 | 6/2014 |
| WO | WO 2014-151363 | 9/2014 |

OTHER PUBLICATIONS

Matijevic, "Surface & Colloid Science," 1973, vol. 6, pp. 23-29.
Temel "Photopolymerization and photophysical properties of amine linked benzophenone photoinitiators for free radical polymerization", Journal of Photochemistry and Photobiology A: Chemistry, 2011, vol. 219 pp. 26-31.
International Search report for PCT International Application No. PCT/US2014/033254 mailed on Sep. 12, 2014, 5 pages.

* cited by examiner

*Primary Examiner* — Michael Pepitone
(74) *Attorney, Agent, or Firm* — Kent S. Kokko

(57) ABSTRACT

Provided are novel high refractive index monomers, and dental resins containing the same.

19 Claims, No Drawings

US 9,675,529 B2

DENTAL COMPOSITION CONTAINING HIGH REFRACTIVE INDEX MONOMERS

CROSS REFERENCE TO RELATED APPLICATIONS

This application is a national stage filing under 35 U.S.C. 371 of PCT/US2014/033254, filed Apr. 8, 2014, which claims priority to U.S. Application No. 61/811,852, filed Apr. 15, 2013 and U.S. Application No. 61/811,850, filed Apr. 15, 2013, the disclosure of which is incorporated by reference in its/their entirety herein.

FIELD OF THE INVENTION

The present disclosure provides novel high refractive index monomers, and dental resins containing the same.

BACKGROUND

Dental composites made from organic resins and filler are finding increasing use in dental applications, especially in restorative dentistry, due to their excellent aesthetic properties. Dental materials generally have unique requirements as compared to the broad spectrum of composite materials. For health reasons, dental materials should be suitable for use in the oral environment. In certain instances, durability of a dental material is important to ensure satisfactory performance. For example, high strength and durability is desirable for dental work that is performed at dentition locations where mastication forces are generally great. In other instances, aesthetic character or quality is highly desired. This is often the case where dental work is performed at locations where a tooth repair or restoration can be seen from a relatively short distance.

It is also generally desired that the dental restorative material blend well with the surrounding dentition and that the dental restorative material looks life-like. Aesthetic quality in dental materials is typically achieved by creating material that has tooth-like colors/shades. Many fillers, however, generally have less mechanical strength than is desired.

Translucency of a dental material is useful for esthetic reasons and for efficient UV curing of the resin. To achieve good translucency, it is desirable to minimize the scattering of light as it passes through the material. This may be accomplished by matching the average refractive index of the filler and the resin.

SUMMARY

The present disclosure provides novel high refractive index monomers that may be blended with dental resins to raise the refractive index thereof, and enable matching of the refractive index of the resin with that of the filler. It has been observed that incorporation of high refractive index groups increases the depth of cure during a UV/Vis-initiated polymerization process by reducing light-scattering due to mismatched refractive indices.

The resins useful for the dental materials of the invention are UV/Vis-curable resins capable of being hardened to form a polymer network such as, for example, acrylate resins, methacrylate resins, epoxy resins, vinyl resins or mixtures thereof. Preferably, the hardenable resin is made from one or more matrix-forming oligomer, monomer, or polymer, or blends thereof. In a preferred embodiment where the dental material of the invention is a dental composite, polymerizable resins suitable for use include hardenable organic resins having sufficient strength, hydrolytic stability, and non-toxicity to render them suitable for use in the oral environment.

In some embodiments the dental resin comprises, in addition to the high refractive index monomer, an addition-fragmentation agent to reduce the stress during polymerization. UV-cured methacrylate restoratives can exhibit significant shrinkage during photopolymerization, which can lead to the build-up of stress within the composite and at the composite-tooth interface. These stresses can become high enough to result in cusp fracture, marginal failure, and/or post-operative sensitivity. The addition-fragmentation agents may be added to polymerizable monomer mixtures to reduce the polymerization-induced stresses.

As used herein:

"dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

"dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"curable" is descriptive of a material or composition that can be polymerized or crosslinked by a free-radical means such as by irradiating with actinic irradiation to induce polymerization and/or crosslinking; "hardened" refers to a material or composition that has been cured (e.g., polymerized or crosslinked).

"initiator" refers to something that initiates curing of a resin. An initiator may include, for example, a polymerization initiator system, a photoinitiator system, a thermal initiator and/or a redox initiator system.

"self-etching" composition refers to a composition that bonds to a dental structure surface without pretreating the dental structure surface with an etchant. Preferably, a self-etching composition can also function as a self-primer wherein no separate etchant or primer is used.

a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

a "dental structure surface" refers to tooth structures (e.g., enamel, dentin, and cementum) and bone.

an "uncut" dental structure surface refers to a dental structure surface that has not been prepared by cutting, grinding, drilling, etc.

an "untreated" dental structure surface refers to a tooth or bone surface that has not been treated with an etchant, primer, or bonding agent prior to application of a self-etching adhesive or a self-adhesive composition of the present invention.

an "unetched" dental structure surface refers to a tooth or bone surface that has not been treated with an etchant prior to application of a self-etching adhesive or a self-adhesive composition of the present invention.

"(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"alkyl" includes straight-chained, branched, and cycloalkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monvalent alkyl or polyvalent alkylene.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene.

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene.

"(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

DETAILED DESCRIPTION

Presently described are dental compositions, dental articles, and methods of use. The dental composition comprises a high refractive index monomer of the formula:

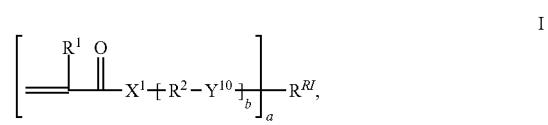

wherein
$R^1$ is H or $C_1$-$C_4$ alkyl,
$X^1$ is —O— or —$NR^1$—,
$R^2$ is an alkylene, optionally substituted by a hydroxyl group;
a is 1 or 2;
b is 0 or 1, preferably 1;
$Y^{10}$ is —O—, —$NR^3$—, —O—CO—, —$NR^3$—CO—, —$NR^3$—CO—NH—, NH—CO—O—, or —O—CO—NH—, where $R^3$ is H, $C_1$-$C_4$ alkyl or

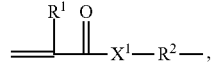

and
$R^{RI}$ is a high refractive index group.

In some preferred embodiments $R^2$ is an alkylene of the formula —($C_tH_{2t}$)— where t is 2 to 10, said group optionally substituted by a hydroxy, i.e. —[$C_tH_{2t-1}$(OH)], such as 2-hydroxypropylene.

In other preferred embodiments, $Y^{10}$ is $Y^{11}$, which is selected from —O—CO—, —$NR^3$—CO—, NH—CO—O—, or —O—CO—NH—, where $R^3$ is H, $C_1$-$C_4$ alkyl or

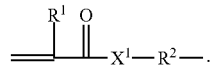

Useful high refractive functional groups include phenyl, benzyl, 2-, 3-, and 4-biphenyl, 1-, 2-, 3-, 4-, and 9-fluorenyl, 4-(1-methyl-1-phenethyl)phenoxyethyl; phenylthio; 1-, 2-, 3- and 4-napthyl, 1- and 2-naphthylthio; 2,4,6-tribromophenoxy; 2,4-dibromophenoxy; 2-bromophenoxy; 1-, and 2-naphthyloxy; 3-phenoxy-; 2-, 3- and 4-phenylphenoxy; 2,4-dibromo-6-sec-butylphenyl; 2,4-dibromo-6-isopropylphenyl; 2,4-dibromophenyl; pentabromobenzyl and pentabromophenyl. As result of the high refractive index group, the homopolymers of the monomers of Formula I have a refractive index of at least 1.50, as measured by an Abbé refractometer. Generally, the high refractive index monomer is added to the dental resins in amounts sufficient to match the refractive index of the resin to the filler. In some embodiments the high refractive index monomer is added in amounts such that the refractive index of the resulting dental resin is of ≥1.50.

The compounds of Formula I where Y is —O—CO—, —$NR^3$—CO—, or —O—CO—NH— are generally prepared by the reaction of an acyl functional compound having the high refractive index aryl group (including acid, ester or acyl halide functional groups) or isocyanate functional compound having the high refractive index aryl group, with an acryloyl compound having a nucleophilic functional group. As evident from Formula I, compounds corresponding to a=1 have one acyl or isocyanate group and compounds where a=2 have two such groups.

More specifically a compound of the formula:

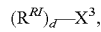    II where $R^{RI}$ comprises high refractive index group, d is 1 or 2, and $X^3$ is a acid, ester, acyl halide or isocyanate group, may be reacted with a compound of the formula:

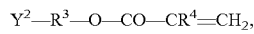    III where $Y^2$ is an nucleophilic functional group reactive with electrophilic $X^3$ groups, $R^3$ is (hetero)hydrocarbyl group, preferably alkylene, and $R^4$ is H or $C_1$-$C_4$ alkyl. The reaction between the $X^3$ and $Y^2$ groups produces the $Y^{10}$ functional group of Formula I.

Where the reactive functional group $X^3$ is an isocyanato functional group, the co-reactive functional $Y^2$ group preferably comprises an amino or hydroxyl group. Where the reactive functional group $X^3$ comprises a carboxyl, ester or acyl halide group, the co-reactive functional $Y^2$ group preferably comprises a hydroxyl, amino, epoxy, isocyanate, or oxazolinyl group.

In some preferred embodiments, the compound of Formula III is carboxy substituted, and reacted with glycidyl methacrylate of Formula III to form a compound where $R^2$ of Formula I is 2-hydroxypropylene.

In other embodiments, compounds of Formula I where $Y^{10}$=—O— or —$NR^3$— can be prepared by reaction of an amine- or hydroxy-functional high refractive index compound (such as napthylamine or hydroxynaphthol) of the formula:

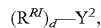    IV where $Y^2$ is a nucleophilic functional group and d is 1 or 2, with a (meth)acrylate compound having a co-reactive functional group of the formula:

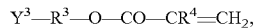    V, where
$Y^3$ is a halide, an isocyanate or an ester functional group $R^3$ is (hetero)hydrocarbyl group, preferably alkylene, and $R^4$ is H or $C_1$-$C_4$ alkyl.

The present disclosure further provides curable dental compositions comprising the high refractive index monomer of Formula I. Although various curable dental compositions have been described, industry would find advantage in compositions having improved properties such as reduced stress while maintaining sufficient mechanical properties and depth of cure. In some embodiments the dental composition further comprises an addition-fragmentation agent reduced polymerization stress.

The polymerizable resin portion of the curable dental composition described herein comprises at least 1 part by weight of high refractive index monomer(s) relative to 100 parts by weight of dental resin. Generally, the amount of high refractive index monomer(s) is from about 1 to 50 parts by weight, preferably 5 to 20 parts by weight, relative to 100 parts by weight of the dental resin.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

The curable compositions described herein further comprise at least one ethylenically unsaturated resin monomer or oligomer in combination with the high refractive index monomer(s). In some embodiments, such as primers, the ethylenically unsaturated monomer may be monofunctional, having a single (e.g. terminal) ethylenically unsaturated group. In other embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

The amount of curable resin in the dental composition is a function of the desired end use (adhesives, cements, restoratives, etc.) and can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

In favored embodiments, such ethylenically unsaturated groups of the curable dental resin includes (meth)acryloyl such as (meth)acrylamide and (meth)acrylate. Other ethylenically unsaturated polymerizable groups include vinyl and vinyl ethers. The ethylenically unsaturated terminal polymerizable group(s) is preferably a (meth)acrylate group, particularly for compositions that are hardened by exposure to actinic (e.g. UV and visible) radiation. Further, methacrylate functionality is typically preferred over the acrylate functionality in curable dental compositions. The ethylenically unsaturated monomer may comprise various ethylenically unsaturated monomers, as known in the art, for use in dental compositions.

In favored embodiments, the (e.g. dental) composition comprises one or more dental resins having a low volume shrinkage monomer. Preferred (e.g. filled) curable dental compositions (useful for restorations such as fillings and crowns) comprise one or more low volume shrinkage resins such that the composition exhibits a Watts Shrinkage of less than about 2%, preferably no greater than 1.80%, more no greater than 1.60%. In favored embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

Preferred low volume shrinkage monomers include isocyanurate resins, such as described in U.S.S.N. 2013/0012614 (Abuelyaman et al.); tricyclodecane resins, such as described in WO 2012/112321 (Abuelyaman et al.); polymerizable resins having at least one cyclic allylic sulfide moiety such as described in U.S. Pat. No. 7,888,400 (Abuelyaman et al.); methylene dithiepane silane resins as described in U.S. Pat. No. 6,794,520 (Moszner et al.); and di-, tri, and/or tetra-(meth)acryloyl-containing resins such as described in U.S. 2010/021869 (Abuelyaman et al.); each of which are incorporated herein by reference.

In favored embodiments, the majority of the (e.g. unfilled) polymerizable resin composition comprises one or more low volume shrinkage monomers ("Low shrinkage monomers"). For example, at least 50%, 60%, 70%, 80%, 90% or more of the (e.g. unfilled) polymerizable resin may comprise low volume shrinkage monomer(s).

In one embodiment, the dental composition comprises at least one isocyanurate resin. The isocyanurate resin comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated (e.g. free radically) polymerizable groups are generally bonded to the core or backbone unit via a (e.g. divalent) linking group.

The trivalent isocyanurate core structure generally has the formula:

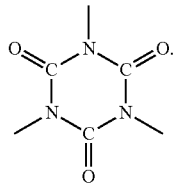

The divalent linking group comprises at least one nitrogen, oxygen or sulfur atom. Such nitrogen, oxygen or sulfur atom forms an urethane, ester, thioester, ether, or thioether linkage. Ether and especially ester linkages can be beneficial over isocyanurate resin comprising urethane linkages for providing improved properties such as reduced viscosity, and/or increased mechanical properties, e.g., diametral tensile strength (DTS). Thus, in some embodiments, the divalent linking groups of the isocyanurate resin are free of urethane linkages. In some favored embodiments, the divalent linking group comprises an ester linkage such as an aliphatic or aromatic diester linkage.

The isocyanurate monomer typically has the general structure:

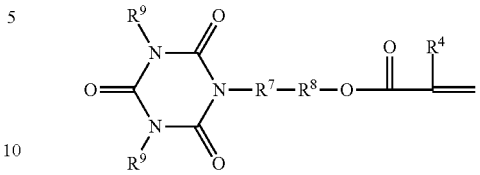

wherein $R^7$ is a (hetero)hydrocarbyl group including straight chain, branched or cyclic alkylene, arylene, or alkarylene, and optionally including a heteroatom (e.g. oxygen, nitrogen, or sulfur); $R^4$ is hydrogen or $C_1$-$C_4$ alkyl; $R^8$ is heterohydrocarbyl group including alkylene, arylene, or alkarylene linking group comprising at least one moiety selected from urethane, ester, thioester, ether, or thioether, and combinations of such moieties; and at least one of the $R^9$ groups is

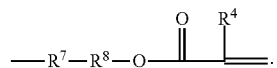

$R^7$ is typically a straight chain, branched or cyclic alkylene, optionally including a heteroatom, having no greater than 12 carbons atoms. In some favored embodiments, $R^7$ has no greater than 8, 6, or 4 carbon atoms. In some favored embodiments, $R_7$ comprises at least one hydroxyl moiety.

In some embodiments, $R^8$ comprises an aliphatic or aromatic ester linkage such as a diester linkage.

In some embodiment, $R^8$ further comprises one or more ether moieties. Hence, the linking group may comprise a combination of ester or diester moieties and one or more ether moieties.

For embodiments, wherein the isocyanurate monomer is a di(meth)acrylate monomer, $R^9$ is hydrogen, alkyl, aryl, or alkaryl, optionally including a heteroatom.

The polymerizable resin portion of the curable unfilled dental composition described herein may comprise at least 10 wt. %, 15 wt. %, 20 wt. %, or 25 wt. %, multifunctional ethylenically unsaturated isocyanurate resin(s). The isocyanurate resin may comprise a single monomer or a blend of two or more isocyanurate resins. The total amount of isocyanurate resin(s) in the unfilled polymerizable resin portion of the curable dental composition is typically no greater than 90 wt. %, 85 wt. %, 80 wt. %, or 75 wt. %.

The filled curable dental composition described herein typically comprises at least 5 wt. %, 6 wt. %, 7 wt. %, 8 wt. %, or 9 wt. % of multifunctional ethylenically unsaturated isocyanurate resin(s). The total amount of isocyanurate resin(s) of the filled hardenable (i.e. polymerizable) dental composition is typically no greater than 20 wt. %, or 19 wt. %, or 18 wt. %, or 17 wt. %, or 16 wt. %, or 15 wt. %.

In another embodiment, the dental composition comprises at least one tricyclodecane resin. The tricyclodecane resin may comprise a single monomer or a blend of two or more tricyclodecane resins. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

Tricyclodecane monomers generally have the core structure (i.e. backbone unit (U):

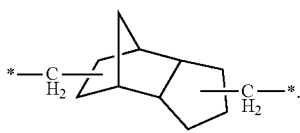

The backbone unit (U) if the tricyclodecane resin typically comprises one or two spacer unit(s) (S) bonded to the backbone unit (U) via an ether linkage. At least one spacer unit (S) comprises a $CH(R^{10})$—OG chain, wherein each group G comprises a (meth)acrylate moiety and R10 (comprises at least one group selected from hydrogen, alkyl, aryl, alkaryl and combinations thereof. In some embodiments, $R^{10}$ is hydrogen, methyl, phenyl, phenoxymethyl, and combinations thereof. G may be bonded to the spacer unit(s) (S) via a urethane moiety.

In some embodiments, the spacer unit(s) (S) typically comprise

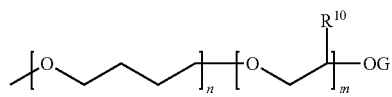

wherein m is 1 to 3; n is 1 to 3; and $R^{10}$ is hydrogen, methyl, phenyl, phenoxymethyl.

In other embodiments, the spacer unit(s) (S) typically comprise

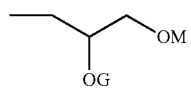

wherein M = aryl.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

In some embodiments, the curable dental composition comprises a polymerizable resin having at least one cyclic allylic sulfide moiety with at least one (meth)acryloyl moiety.

The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth)acrylate moiety) or a (meth)acryloylamino (i.e., a (meth)acrylamide moiety).

In one embodiment, the low shrinkage resin includes those represented by the formulae:

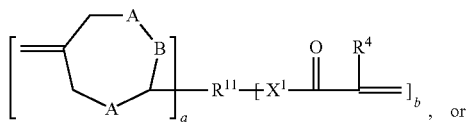, or

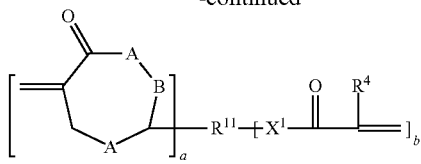

In the above formulae, each A can be independently selected from S, O, N, C (e.g.,) $C(R^{10})_2$, where each $R^{10}$ is independently a H or an organic group), SO, $SO_2$, N-alkyl, N-acyl, NH, N-aryl, carboxyl or carbonyl group, provided that at least one X is S or a group comprising S. Preferably, each A is sulfur.

B is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with B thus being either absent or methylene, respectively. In some embodiments, B is either absent or is a $C_1$ to $C_3$ alkylene, optionally including a heteroatom, carbonyl, acyl, or combinations thereof.

$X^1$ is independently —O— or —$NR^4$—, where $R^4$ is H or $C_1$-$C_4$ alkyl.

The $R^{11}$ group represents a linker selected from alkylene (typically having more than one carbon atom, i.e. excluding methylene), alkylene optionally including a heteroatom (e.g., O, N, S, S—S, SO, $SO_2$), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

$R^4$ is H or $C_1$-$C_4$ alkyl, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

The inclusion of a polymerizable compound having at least one cyclic allylic sulfide moiety can result in a synergistic combination of low volume shrinkage in combination with high diametral tensile strength.

In another embodiment, the dental composition comprises a low shrinkage resin that includes at least one di-, tri-, and/or tetra(meth)acryloyl-containing resins having the general formula:

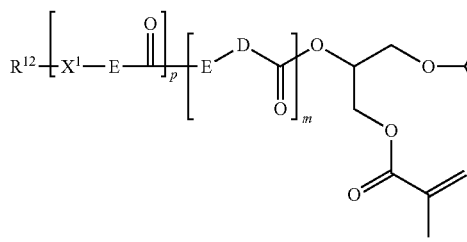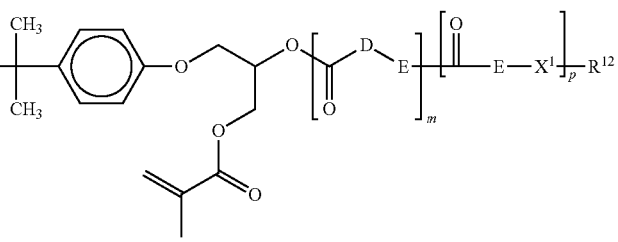

wherein: each $X^1$ is independently —O— or —NR$^4$—, where $R^4$ is H or $C_1$-$C_4$ alkyl;
D and E each independently represent an organic group, and $R^{12}$ represents —C(O)C(CH$_3$)=CH$_2$, and/or p=0 and $R^{12}$ represents H, —C(O)CH=CH$_2$, or —C(O)C(CH$_3$)=CH$_2$, with the proviso that at least one $R^{12}$ is a (meth)acrylate; each m is 1 to 5; p and q are independently 0 or 1. Although, this material is a derivative of bisphenol A, when other low volume shrinkage monomer are employed, such as the isocyanurate and/or tricyclodecane monomer, the dental composition is free of (meth)acrylate monomers derived from bisphenol A. Such resins are described in WO 2008/082881 (Abuelyaman et al.)

In another embodiment, the low shrinkage dental resin may be selected from methylene dithiepane silane resins described in U.S. Pat. No. 6,794,520 (Moszner et al.), incorporated herein by reference. Such resins have the general formula

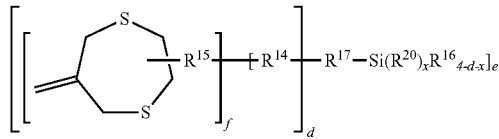

in which $R^{14}$ is a saturated or unsaturated aliphatic or alicyclic hydrocarbon radical with 1 to 10 carbon atoms, which can be interrupted by one or more oxygen and/or sulfur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^{15}$ has one of the meanings given for $R^{14}$ or is absent; $R^{16}$ has one of the meanings given for $R^{14}$ or is absent; $R^{17}$ is equal to —(CHR$^{19}$)$_n$—, —W—CO—NH—(CHR$^{19}$)$_n$—, —Y—CO—NH—R$^{18}$—, —(CHR$^{19}$)$_n$—, —SR$^{18}$—, —CO—O—R$^{18}$— or is absent, with n being equal to 1 to 4, $R^{19}$ is hydrogen, $C_1$ to $C_{10}$ alkyl or $C_6$ to $C_{10}$ aryl, $R^{18}$ has one of the meanings given for $R^{14}$ and W stands for an O or S atom or is absent; with $R^{18}$ and $R^{19}$ being able to be substituted or unsubstituted; $R^{20}$ is a hydrolyzable group; d, e, f and x each independently of each other being 1, 2 or 3; and the sum of d+x=2 to 4.

The multifunctional low shrink resins are (e.g. highly) viscous liquids at about 25° C., yet are flowable. The viscosity as can be measured with a Haake RotoVisco RV1 device, as described in EP Publication No. 2401998, published Jan. 2, 2012 is typically at least 300, or 400, or 500 Pa*s and no greater than 10,000 Pascal-seconds (Pa*s). In some embodiments, the viscosity is no greater than 5000 or 2500 Pa*s.

The ethylenically unsaturated resins of the dental composition are typically stable liquids at about 25° C. meaning that the resins do not substantially polymerize, crystallize, or otherwise solidify when stored at room temperature (about 25° C.) for a typical shelf life of at least 30, 60, or 90 days. The viscosity of the resins typically does not change (e.g. increase) by more than 10% of the initial viscosity.

Particularly for dental restoration compositions, the ethylenically unsaturated resins generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight resin lacking such substituents).

In some embodiments, the (unfilled) polymerizable resin may comprise solely one or more low shrink resins in combination with the addition fragmentation agent(s). In other embodiments, the (unfilled) polymerizable resin comprises a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt. %, 19 wt. %, 18 wt. %, 17 wt. %, 16 wt. %, or 15 wt. % of the (unfilled) polymerizable resin portion. The concentration of such other monomers is typically no greater than 5 wt. %, 4 wt. %, 3 wt. %, or 2 wt. % of the filled polymerizable dental composition.

In some embodiments, the "other monomers" of the dental composition comprise a low viscosity reactive (i.e. polymerizable) diluent. Reactive diluents typically have a viscosity of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent
comprises one or two spacer unit(s) (S) being connected to the backbone unit (U) via an ether linkage; such as described in WO 2012/112321 (Abuelyaman et al.).

The curable component of the curable dental composition can include a wide variety of "other" ethylenically unsaturated compounds (with or without acid functionality), epoxy-functional (meth)acrylate resins, vinyl ethers, and the like.

The (e.g., photopolymerizable) dental compositions may include free radically polymerizable monomers, agents, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl(meth)acrylate, ethyl(meth)acrylate, isopropyl(meth)acrylate, n-hexyl(meth)acrylate, stearyl (meth)acrylate, allyl(meth)acrylate, glycerol tri(meth) acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth) acrylate, 1,2,4-butanetriol tri(meth)acrylate, 1,4-cyclohexanediol di(meth)acrylate, pentaerythritol tetra(meth) acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone(meth) acrylamide; urethane(meth)acrylates; the bis-(meth) acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups as an example of an "other monomer". Examples of such materials include hydroxyalkyl(meth)acrylates, such as 2-hydroxyethyl(meth)acrylate and 2-hydroxypropyl(meth) acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are available from a wide variety of commercial sources, such as Sigma-Aldrich, St. Louis.

The curable dental compositions can include at least 1 wt. %, at least 3 wt. %, or at least 5 wt. % ethylenically unsaturated compounds with hydroxyl functionality, based on the total weight of the unfilled composition. The compositions can include at most 80 wt. %, at most 70 wt. %, or at most 60 wt. % ethylenically unsaturated compounds with hydroxyl functionality.

The dental compositions described herein may include one or more curable components in the form of ethylenically unsaturated compounds with acid functionality as an example of an "other" monomer. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. Such acid-functional "other" monomers contribute to the self-adhesion or self-etching of the dental compositions as described in U.S. Pat. No. 7,452,924 and U.S. Pat. No. 7,449,499 (Falsafi et al.), incorporated herein by reference.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth) acrylate (e.g., HEMA) phosphates, bis((meth)acryloxyethyl) phosphate, bis((meth)acryloxypropyl)phosphate, bis((meth) acryloxy)propyloxy phosphate, (meth)acryloxyhexyl phosphate, bis((meth)acryloxyhexyl)phosphate, (meth)acryloxyoctyl phosphate, bis((meth)acryloxyoctyl)phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly (meth)acrylated polyboric acid, and the like, may be used as components. Also monomers, oligomers, and polymers of unsaturated carbonic acids such as (meth)acrylic acids, itaconic acid, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth) acryloxy group and at least one —O—$P(O)(OH)_x$ group, wherein x=1 or 2, and wherein the at least one —O—P(O) $(OH)_x$ group and the at least one (meth)acryloxy group are linked together by a $C_1$-$C_4$ hydrocarbon group; a second compound including at least one (meth)acryloxy group and at least one —O—$P(O)(OH)_x$ group, wherein x=1 or 2, and wherein the at least one —O—$P(O)(OH)_x$ group and the at least one (meth)acryloxy group are linked together by a $C_5$-$C_{12}$ hydrocarbon group; an ethylenically unsaturated compound without acid functionality; an initiator system; and a filler.

The curable dental compositions can include at least 1 wt. %, at least 3 wt. %, or at least 5 wt. % ethylenically unsaturated compounds with acid functionality, based on the total weight of the unfilled composition. The compositions can include at most 80 wt. %, at most 70 wt. %, or at most 60 wt. % ethylenically unsaturated compounds with acid functionality.

The curable dental compositions may include resin-modified glass ionomer cements such as those described in U.S. Pat. No. 5,130,347 (Mitra), U.S. Pat. No. 5,154,762 (Mitra), U.S. Pat. No. 5,925,715 (Mitra et al.) and U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the mixture of polymerizable ingredients (i.e. curable resins and the addition-fragmentation agent of Formula I). The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the mixture of resins is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroborate. Some preferred photosensitizers may include monoketones and diketones (e.g. alpha diketones) that absorb some light within a range of about 300 nm to about 800 nm (preferably, about 400 nm to about 500 nm) such as camphorquinone, 1-phenyl-1,2-propanedione, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl) phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photoinitiator may also be a polymerizable photoinitiator having a free-radically polymerizable groups and a photoinitiator group. Such polymerizable photoinitiators include 4-benzoylphenyl acrylate, 2-(4-benzoylphenoxy) ethyl acrylate and 2-[4-(2-hydroxy-2-methylpropanoyl)phenoxy]ethyl-N-acryloyl-2-methylalinate, and are described in U.S. Pat. No. 7,838,110 (Zhu et al.), U.S. Pat. No. 5,506,279 (Babu et al.), incorporated herein by reference, and also Temel et al. "Photopolymerization and photophysical properties of amine linked benzophenone photoinitiators for free radical polymerization", Journal of Photochemistry and Photobiology A, Chemistry 219 (2011), pp. 26-31.

The initiator is used in an amount effective to facilitate free radical addition to the addition-fragmentation crosslinking agent and the amount will vary depending upon, e.g., the type of initiator and the molecular weight of the polymer and the degree of functionalization desired. The initiators can be used in amounts from about 0.001 part by weight to about 5 parts by weight based on 100 parts total monomer.

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture.

Curing is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 500-1500 mW/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically curable, i.e., the compositions contain a chemical initiator (i.e., initiator system) that can polymerize, cure, or otherwise harden the composition without dependence on irradiation with actinic radiation. Such chemically curable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluene-sulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mita et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile, as well as dicumyl peroxide, which is favored for mill blanks.

In favored embodiments, such as when the dental composition is employed as a dental restorative (e.g. dental filling or crown) or an orthodontic cement, the dental composition typically comprises appreciable amounts of (e.g. nanoparticle) filler. The amount of such fillers is a function of the end use as further described herein. Such compositions preferably include at least 40 wt. %, more preferably at least 45 wt. %, and most preferably at least 50 wt. % filler, based on the total weight of the composition. In some embodiments the total amount of filler is at most 90 wt. %, preferably at most 80 wt. %, and more preferably at most 75 wt. % filler.

The (e.g. filled) dental composite materials typically exhibit a diametral tensile strength (DTS) of at least about 70, 75, or 80 MPa and/or a Barcol Hardness of at least about 60, or 65, or 70. The ISO 4049 depth of cure ranges from about 4 to about 5 mm and is comparable to commercially available (e.g. filled) dental compositions suitable for restorations.

Dental compositions suitable for use as dental adhesives can optionally also include filler in an amount of at least 1 wt. %, 2 wt. %, 3 wt. %, 4 wt. %, or 5 wt. % based on the total weight of the composition. For such embodiments, the total concentration of filler is at most 40 wt. %, preferably at most 20 wt. %, and more preferably at most 15 wt. % filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Suitable inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as U.S. Pat. No. 6,387,981 (Zhang et al.), U.S. Pat. No. 6,730,156 (Windisch et al.), U.S. Pat. No. 6,899,948 (Zhang et al.), and U.S. Pat. No. 7,393,882 (Wu et al.). Filler components described in these references include nanosized silica particles, nanosized metal oxide particles, and combinations thereof. Nanofillers are also described in U.S. Pat.

No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 75 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1041, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO™ 1042 or 2327.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The primary particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like and may comprise silane, zirconate or titanate coupling agents. Preferred coupling agents include gamma-methacryloxypropyltrimethoxysilane, gamma-mercaptopropyltriethoxysilane, gamma-aminopropyltrimethoxysilane, and the like.

Suitable copolymerizable or reactive organometallic compounds may have the general formulas: $CH_2\!\!=\!\!C(R^{22})\!-\!R^{21}Si(OR)\!-\!R_{3-n}$ or $CH_2\!\!=\!\!C(R^{22})\!-\!C\!\!=\!\!OOR^{21}Si(OR)_n R_{3-n}$; wherein R is an $C_1$-$C_4$ alkyl, $R^{21}$ is a divalent organic heterohydrocarbyl linking group, preferably alkylene; $R^{22}$ is H or C1-C4 alkyl; and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, the silica particulate filler may be surface modified by an addition-fragmentation agent, such as are described in Applicant's copending applications U.S. 2012/050718 (Joly et al.) and U.S. Ser. No. 61/725,077 (Joly et al.) each incorporated herein by reference.

In some preferred embodiments the dental composition further comprises an addition-fragmentation agent. The addition-fragmentation agent comprising at least one ethylenically unsaturated terminal group and a backbone unit comprising an α,β-unsaturated carbonyl. The addition-fragmentation agent is free-radically cleavable.

The addition-fragmentation agents are preferably of the following formula:

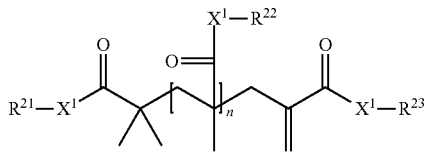

wherein
$R^{21}$, $R^{22}$ and $R^{23}$ are each independently $Z_m$-Q-, a (hetero)alkyl group or a (hetero)aryl group with the proviso that at least one of $R^1$, $R^2$ and $R^3$ is $Z_m$-Q-,
Q is a linking group have a valence of m+1;
Z is an ethylenically unsaturated polymerizable group,
m is 1 to 6, preferably 1 to 2;
each $X^1$ is independently —O— or —$NR^4$—, where $R^4$ is H or $C_1$-$C_4$ alkyl, and
n is 0 or.

Addition-fragmentation agents according to Formula VI are described in U.S. 2012-0208965 (Joly et al.); incorporated herein by reference. Other useful addition fragmentation agents are described in Applicant's copending US2012/050718 (Joly et al.), U.S. 61/725,077 filed 12 Nov. 2012 (Joly et al.); U.S. 61/738,067 filed 17 Dec. 2012 (Fornof et al.); U.S. 61/803,480 filed 20 Mar. 2013 (Moser et al.), and 61/803,481 (Moser et al.)

In some favored embodiments, the addition-fragmentation agents ("AFM") may be added to a dental composition comprising at least one ethylenically unsaturated monomer or oligomer. Without intending to be bound by theory, it is surmised that the inclusion of such addition-fragmentation material reduces the polymerization-induced stresses, such as by the mechanism described in U.S. Publication 2012/0208965. For embodiments wherein the AFM are multifunctional, comprising at least two ethylenically unsaturated group (e.g. Z is ≥2 in Formula VI), the material can function as crosslinking agents, where the crosslinks are labile.

The total amount of addition-fragmentation agent(s) in the polymerizable resin portion of the unfilled curable dental composition is typically no greater than 15 parts by weight, relative to 100 parts by weight of dental resin. As the concentration of the addition-fragmentation monomer increases, the stress deflection and Watts Shrinkage typically decrease. However, when the amount of addition-fragmentation agent exceeds an optimal amount, mechanical properties such as Diametral tensile strength and/or Barcol hardness, or depth of cure may be insufficient.

The polymerizable resin portion of the curable dental composition described herein comprises at least 0.1 parts by weight of addition-fragmentation agent(s). Generally, the amount of addition-fragmentation agent is from about 0.5 to 10 parts by weight relative to 100 parts by weight of dental resin.

The present disclosure provides stable curable composition that provides enhanced optical translucency. In one embodiment, the present invention features a hardenable dental composition comprising a dental resin, the high refractive index monomer, a filler, and preferably the addition-fragmentation agent. The combined mixture is generally within 4 percent of the refractive index of the filler and/or resin, typically within 3 percent thereof, more typically within 1 percent thereof, and even more typically within 0.5 percent thereof. The refractive index of the combined mixture may be measured in the hardened state or the unhardened state.

EXAMPLES

As used herein, the term AFM refers to addition fragmentation agents. Unless otherwise specified, all percentages are by weight.

Test Methods

Depth of Cure Test Method (DOC)

The depth of cure (DOC) was measured for a test sample composition after curing. A test fixture with an open 8 millimeter stainless steel mold cavity was placed on a polyester film and filled with the sample composition. A second polyester film placed atop the resin and fixture was pressed to provide a level surface on the composition. The filled test fixture was placed on a white background surface and the composition was irradiated for 20 seconds using a dental curing light (3M Dental Products Curing Light 2500 or 3M ESPE Elipar FreeLight2, 3M ESPE Dental Products). After curing, the sample was removed from the mold and the uncured resin was gently removed, e.g., gently scraping materials from the bottom of the sample which was the side that was not irradiated with the curing light. The thickness of the remaining cured material was measured. The reported depths are the actual cured thickness in millimeters divided by 2.

Stress Test Method (Cusp Deflection)

This test measures the stress development during the curing process. A test fixture was prepared by machining a slot into a rectangular 15 mm×8 mm×8 mm aluminum block. The slot was 8 mm long, 2.5 mm deep, and 2 mm across, and was located 2 mm from an edge, thus forming a 2 mm wide aluminum cusp adjacent to a 2 mm wide cavity containing the test compositions. A linear variable displacement transducer (Model GT 1000, used with an E309 analog amplifier (RDP Electronics, United Kingdom) was positioned to measure the displacement of the cusp tip as the dental composition was photocured at room temperature. Prior to testing, the slot in the aluminum block was sandblasted using Rocatec Plus Special Surface Coating Blasting Material (3M ESPE), treated with RelyX Ceramic Primer (3M ESPE), and finally treated with a dental adhesive, Adper Easy Bond (3M ESPE).

The slot was fully packed with the composition, which equaled approximately 100 mg of material. The material was irradiated for 1 minute with a dental curing lamp (Elipar S-10, 3M ESPE) positioned almost in contact (less than 1 mm) with the material in the slot. The displacement of the cusp in microns was recorded 9 minutes after the lamp was extinguished.

Materials.

Commercial reagents were used as received. When not specified, reagents were obtained from Sigma Aldrich or EMD.

2-Aminobiphenyl

2-Biphenyl carboxylic acid 4-(Dimethylamino)pyridine

AFM-1—prepared as described in U.S. Patent Application No. 2012-0208965, "Addition-Fragmentation Agents" (67046US003)

BisGMA—(2,2-Bis[4-(2-hydroxy-3-methacryloyloxy-propoxy)phenyl]propane, Sigma Aldrich, St. Louis, Mo., USA
CPQ—camphorquinone
$CH_2Cl_2$—Dichloromethane—EMD Chemicals Inc.; Gibbstown, N.J., USA
Diethanolamine
Diphenic acid
DPIPF6—Diphenyliodonium hexafluorophosphate (≥98%),
EDMAB—Ethyl 4-N,N-dimethylamino benzoate,
EtOAc—ethyl acetate—EMD Chemicals Inc.; Gibbstown, N.J., USA
Glycidyl methacrylate—
HEMA—2-Hydroxyethyl methacrylate,
Hexane—EMD Chemicals Inc.; Gibbstown, N.J., USA
$MgSO_4$—Magnesium sulfate
MEHQ
Methacrylic anhydride
Methacryloyl chloride
MHP—6-methacryloyloxyhexyl phosphate—compound preparation described in U.S. 2009/0011388 (Craig, et al.)
Oxalyl chloride
$SiO_2$—silica gel, 230-400 mesh—Alfa Aesar, Ward Hill, Mass.
Sodium bicarbonate
Sodium chloride
Triethylamine
UDMA—Rohamere™ 6661-0 (diurethane dimethacrylate, CAS No. 41 137-60-4), Rohm Tech, Inc., Malden, Mass.
$YbF_3$—Ytterbium(III) fluoride,
Z250 filler—filler prepared according to Example 1 of U.S. Pat. No. 4,503,169, incorporated herein in its entirety by reference Instrumentation Nuclear magnetic resonance spectra (proton—$^1$H NMR) were analyzed and recorded using an NMR spectrometer (UltraShield™Plus 500 MHz NMR spectrometer; Bruker Corporation; Billerica, Mass.).

Refractive Indices were measured at room temperature on a refractometer manufactured by Bausch & Lomb (Rochester, N.Y., USA) Cat. No. 33.46.10.

Example 1

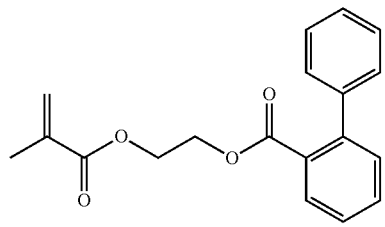 [SMILES: C=C(C)C(=O)OCCOC(=O)c1ccccc1-c1ccccc1]

A solution of oxalyl chloride (9.33 g, 73.5 mmol, 1.05 eq.) in 50 mL $CH_2Cl_2$ was added dropwise via addition funnel to a solution of 2-biphenyl carboxylic acid (14.57 g, 73.5 mmol, 1.05 eq) in 50 mL $CH_2Cl_2$. The resultant solution was allowed to stir at room temperature overnight under nitrogen atmosphere. The solvents were removed under reduced pressure, and the residue was dissolved in 50 mL $CH_2Cl_2$. A solution of 2-hydroxyethyl methacrylate (9.11 g, 70.0 mmol, 1.0 eq.), triethylamine (10.63 g, 105 mmol, 1.5 eq.) and 4-(dimethylamino)pyridine (0.86 g, 7.0 mmol, 0.1 eq.) in 50 mL $CH_2Cl_2$ was added dropwise via addition funnel. The resultant mixture was allowed to stir at room temperature overnight under nitrogen atmosphere.

The mixture was then sequentially washed with 1N aq. HCl (100 mL), $H_2O$ (100 mL), sat. aq. $NaHCO_3$ (100 mL), and sat. aq. NaCl (100 mL). The organic layer was dried over $MgSO_4$, filtered, and concentrated to a yellow oil. This crude material was purified via a suction filter column ($SiO_2$, 9/1 hexane/EtOAc eluent). Approximately 250 ppm MEHQ was added to the combined product fractions, which were concentrated to a clear, pale yellow viscous syrup. Final drying was accomplished by bubbling air through the syrup for 48 hours to provide 19.86 g product (92% of theoretical yield). NMR analyses confirmed the structure of the product.

Example 2

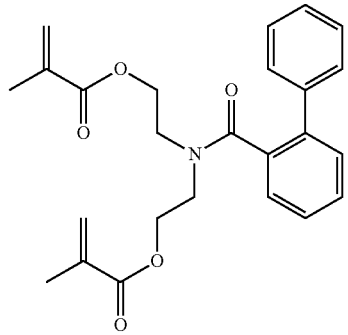 [SMILES: C=C(C)C(=O)OCCN(CCOC(=O)C(=C)C)C(=O)c1ccccc1-c1ccccc1]

A solution of oxalyl chloride (4.00 g, 31.5 mmol, 1.05 eq.) in 20 mL $CH_2Cl_2$ was added dropwise via addition funnel to a solution of 2-biphenyl carboxylic acid (6.24 g, 31.5 mmol, 1.05 eq) in 20 mL $CH_2Cl_2$. The resultant solution was allowed to stir at room temperature overnight under nitrogen atmosphere. The solvents were removed under reduced pressure, and the residue was dissolved in 30 mL $CH_2Cl_2$. This solution was added dropwise via addition funnel to a solution of diethanolamine (3.15 g, 30.0 mmol, 1.0 eq.) and triethylamine (4.55 g, 45.0 mmol, 1.5 eq.) in 30 mL $CH_2Cl_2$, and allowed to stir under nitrogen atmosphere for 3 h. The mixture was then adsorbed onto silica gel and purified via a suction filter column ($SiO_2$, EtOAc eluent).

Concentration of the product fractions affords 6.35 grams of a white solid which $^1$H NMR ($CDCl_3$, 500 MHz) verified to be the desired amide diol intermediate product (74% of theoretical yield). This diol material was dissolved in 50 mL $CH_2Cl_2$, and triethylamine (7.59 g, 75 mmol, 3.4 eq) was added. A solution of methacryloyl chloride (6.98 g, 66.8 mmol, 3.0 eq.) in 30 mL $CH_2Cl_2$ was added dropwise via addition funnel under nitrogen atmosphere and the resultant mixture was allowed to stir overnight. The mixture was then washed sequentially with 1N aq. HCl (50 mL), $H_2O$ (50 mL), sat. aq. $NaHCO_3$ (50 mL), and sat. aq. NaCl (50 mL). The organic layer was dried over $MgSO_4$, filtered, and concentrated to a yellow oil. This crude material was purified via a suction filter column ($SiO_2$, 3/1 hexane/EtOAc eluent). Approximately 250 ppm MEHQ was added to the combined product fractions, which were concentrated to a clear, pale yellow viscous syrup. Final drying was accomplished by bubbling air through the syrup for 48 hours to provide 8.10 g product (86% of theoretical yield). NMR analyses confirmed the structure of the product.

Example 3

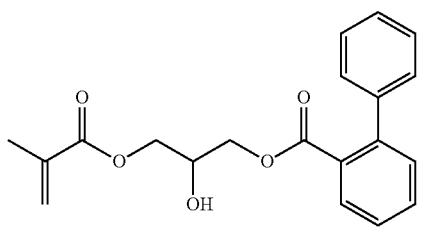 [SMILES: C=C(C)C(=O)OCC(O)COC(=O)c1ccccc1-c1ccccc1]

A 50 mL round-bottomed flask was charged with 2-biphenyl carboxylic acid (1.98 g, 10.0 mmol, 1.0 eq.), glycidyl methacrylate (1.42 g, 10.0 mmol, 1.0 eq.), and triethylamine (0.10 g, 1.0 mmol, 0.1 eq.). The resultant mixture was heated gently overnight with a heating mantle while stirring open to air. The mixture was then adsorbed onto silica gel and purified via a suction filter column ($SiO_2$, 3/1 hexane/EtOAc eluent). Approximately 250 ppm MEHQ was added to the combined product fractions, which were concentrated to a clear, pale yellow viscous syrup. Final drying was accomplished by bubbling air through the syrup for 48 hours to provide 3.03 g product (89% of theoretical yield). NMR analyses confirmed the structure of the product.

Example 4

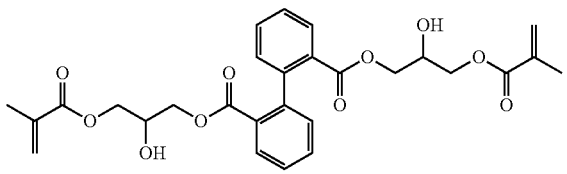 [SMILES: C=C(C)C(=O)OCC(O)COC(=O)c1ccccc1-c1ccccc1C(=O)OCC(O)COC(=O)C(=C)C]

A 200 mL round-bottomed flask was charged with diphenic acid (4.84 g, 20.0 mmol, 1.0 eq.), glycidyl methacrylate (5.69 g, 40.0 mmol, 2.0 eq.), and triethylamine (0.20 g, 2.0 mmol, 0.1 eq.). The resultant mixture was heated gently overnight with a heating mantle while stirring open to air. The mixture was then adsorbed onto silica gel and purified via a suction filter column ($SiO_2$, ramp eluent from 3/1 to 2/1 hexane/EtOAc). Approximately 250 ppm MEHQ was added to the combined product fractions, which were concentrated to a clear, pale yellow viscous syrup. Final drying was accomplished by bubbling air through the syrup for 48 hours to provide 6.98 g product (66% of theoretical yield). NMR analyses confirmed the structure of the product.

Example 5

Preparation of 2-methyl-N-(2-phenylphenyl)prop-2-enamide

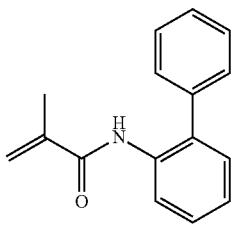 [SMILES: C=C(C)C(=O)Nc1ccccc1-c1ccccc1]

A 250 mL glass jar was charged with 2-aminobiphenyl (30.0 g, 0.18 mol), methacrylic anhydride (31.0 g, 0.20 mol), and 4-(dimethylamino)pyridine (50 mg, 0.4 mmol). The jar was sealed and placed in a 70° C. oven for 3 hours. After cooling to room temperature, the reaction mixture was taken up in 200 mL of methylene chloride and washed with a saturated aqueous solution of $NaHCO_3$ (3×100 mL), The organic layer was dried over magnesium sulfate, filtered, and solvent removed at reduced pressure to leave an orange oil that crystallized on standing. This crude material was purified by chromatography on silica gel eluted with methylene chloride to afford 38.4 g of the desired product. NMR analyses confirmed the structure of the product.

Examples 6-9

Comparative Example C1

Paste compositions suitable for dental resins were prepared by mixing the compositions shown in Table 1 to form uniform dispersions with the high refractive index monomer prepared in Example 1. Amounts shown in the tables are in weight percent. The compositions were tested according to the test method described above for the depth of cure (DOC) in millimeters (mm). Additionally, stress, indicated by cusp deflection, was measured according to the test method described above and is measured in microns. Results are shown in Table 1 below.

Example C1 was prepared and tested in the same manner except that no high refractive index monomer was added.

TABLE 1

|  | C1 | 6 | 7 | 8 | 9 |
| --- | --- | --- | --- | --- | --- |
| $DPIPF_6$ | 0.18 | 0.18 | 0.18 | 0.18 | 0.18 |
| CPQ | 0.14 | 0.14 | 0.14 | 0.14 | 0.14 |
| EDMAB | 0.40 | 0.40 | 0.40 | 0.40 | 0.40 |
| MHP | 9.00 | 8.62 | 8.23 | 7.85 | 7.85 |
| UDMA | 1.20 | 1.15 | 1.09 | 1.04 | 1.04 |
| HEMA | 10.68 | 10.21 | 9.76 | 9.29 | 4.50 |
| bisGMA | 14.40 | 13.80 | 13.20 | 12.60 | 12.60 |
| AFM-1 | 1.00 | 1.00 | 1.00 | 1.00 | 1.00 |
| Example 1 | 0 | 1.50 | 3.00 | 4.50 | 9.29 |
| $YbF_3$ | 5.00 | 5.00 | 5.00 | 5.00 | 5.00 |
| Z250 filler | 58.00 | 58.00 | 58.00 | 58.00 | 58.00 |
| Total % | 100.00 | 100.00 | 100.00 | 100.00 | 100.00 |
| DOC | 3.52 | 3.71 | 3.80 | 3.86 | 3.96 |
| Cusp deflection | 5.20 | n/a | n/a | 4.88 | 3.84 |

Examples 10-21

Paste compositions were prepared and tested as described above for Examples 6-9, except that the high refractive index monomer prepared in Example 2 was used for Examples 10-13, the high refractive index monomer prepared in Example 3 was used for Examples 14-17, and the high refractive index monomer prepared in Example 4 was used for Examples 18-21, instead of the high refractive index monomer prepared in Example 1. Amounts of other materials for each amount of high refractive index monomer remained the same for all three additional examples.

The compositions were tested as described above for depth of cure and cusp deflection. Results are shown in Tables 2, 3, and 4 for high refractive index monomer examples 2, 3, and 4, respectively.

TABLE 2

|                | 1    | 10   | 11   | 12   | 13   |
|----------------|------|------|------|------|------|
| Example 2      | 0    | 1.50 | 3.00 | 4.50 | 9.29 |
| DOC            | 3.52 | 3.77 | 3.85 | 3.86 | 3.99 |
| Cusp deflection| 5.20 | n/a  | n/a  | 4.82 | 2.89 |

TABLE 3

|                | 1    | 14   | 15   | 16   | 17   |
|----------------|------|------|------|------|------|
| Example 3      | 0    | 1.50 | 3.00 | 4.50 | 9.29 |
| DOC            | 3.52 | 3.71 | 3.84 | 3.87 | 3.98 |
| Cusp deflection| 5.20 | n/a  | n/a  | 4.91 | 2.82 |

TABLE 4

|                | 1    | 18   | 19   | 20   | 21   |
|----------------|------|------|------|------|------|
| Example 4      | 0    | 1.50 | 3.00 | 4.50 | 9.29 |
| DOC            | 3.52 | 3.78 | 3.87 | 3.85 | 3.98 |
| Cusp deflection| 5.20 | n/a  | n/a  | 4.83 | 3.43 |

What is claimed is:

1. A curable dental composition comprising:
   a) at least one dental resin comprising at least two ethylenically unsaturated groups;
   b) a high refractive index monomer;
   c) an addition fragmentation agent; and
   d) optionally an inorganic oxide filler,
   said high refractive index monomer is of the formula:

$$\left[ \underset{=}{\overset{R^1}{|}} \overset{O}{\underset{||}{C}} - X^1 + R^2 - Y^{10} \underset{b}{\vphantom{]}} \right]_a R^{RI}, \qquad I$$

wherein
$R^1$ is H or $C_1$-$C_4$ alkyl,
$X^1$ is —O— or —NR$^1$—,
$R^2$ is a alkylene, optionally substituted by a hydroxyl group;
a is 1 or 2;
b is 0 or 1;
$Y^{10}$ is —O—CO—, —NR$^3$—CO—, where $R^3$ is H, $C_1$-$C_4$ alkyl, NH—CO—O—, or —O—CO—NH—, or $$\underset{=}{\overset{R^1}{|}} \overset{O}{\underset{||}{C}} - X^1 - R^2 -,$$

and
$R^{RI}$ is a high refractive index group selected from 2, 3-, and 4-biphenyl, 1-, 2, 3-, 4-, and 9-fluorenyl, 4-(1-methyl-1-phenethyl)phenoxyethyl; phenylthio; 1-, 2-, 3- and 4-napthyl, 1- and 2-naphthylthio; 2,4,6-tribromophenoxy; 2,4-dibromophenoxy; 2-bromophenoxy; 1-, and 2-naphthyloxy; 3-phenoxy-; 2-, 3- and 4-phenylphenoxy; 2,4-dibromo-6-sec-butylphenyl; 2,4-dibromo-6-isopropylphenyl; 2,4-dibromophenyl; pentabromobenzyl and pentabromophenyl.

2. The curable dental composition of claim 1 wherein the addition-fragmentation agent is of the formula:

$$R^{21}-X^1 \overset{O}{\underset{||}{C}} \underset{|}{\overset{X^1-R^{22}}{\underset{|}{C}}} \underset{n}{\vphantom{]}} \overset{O}{\underset{||}{C}} X^1-R^{23} \qquad VI$$

wherein
$R^{21}$, $R^{22}$ and $R^{23}$ are each independently $Z_m$-Q-, a (hetero)alkyl group or a (hetero)aryl group with the proviso that at least one of $R^{21}$, $R^{22}$ and $R^{23}$, is $Z_m$-Q-,
Q is a linking group have a valence of m+1;
Z is an ethylenically unsaturated polymerizable group,
m is 1 to 6;
each $X^1$ is independently —O— or —NR$^1$—, where $R^1$ is H or $C_1$-$C_4$ alkyl, and
n is 0 or 1.

3. The curable dental composition of claim 1 comprising at least 0.1 wt. %, of addition-fragmentation agent.

4. The curable dental composition of claim 1 wherein $R^2$ is —($C_tH_{2t}$)— or —[$C_tH_{2t-1}$(OH)], where t is 2 to 10.

5. The curable dental composition of claim 1 comprising:
   a) 100 parts of at least one dental resin comprising at least two ethylenically unsaturated groups;
   b) 1 to 50 parts by weight of the high refractive index monomer, relative to 100 parts by weight dental resin; and
   c) at least 0.1 parts of addition-fragmentation agent(s), and
   d) optionally an inorganic oxide filler.

6. The curable dental composition of claim 1 further comprising at least 1 part inorganic filler relative to 100 parts of dental resin.

7. The curable dental composition of claim 1 wherein the dental resin comprises an aromatic monomer having a refractive index of at least 1.50.

8. The curable dental composition of claim 1 wherein the dental resin is a low volume shrinkage resin.

9. The curable dental composition of claim 1 wherein the dental resin is an isocyanurate resin, a tricyclodecane resin, cyclic allylic sulfide resins; methylene dithiepane silane resins; and poly(meth)acryloyl-containing resins, or mixtures thereof.

10. The curable dental composition of claim 1 wherein the dental resin further comprises at least one other (meth) acrylate monomer is selected from ethoxylated bisphenol A dimethacrylate, 2-hydroxyethyl methacrylate, bisphenol A diglycidyl dimethacrylate, urethane dimethacrylate, triethlyene glycol dimethacrylate, glycerol dimethacrylate, ethylenegylcol dimethacrylate, neopentylglycol dimethacrylate (NPGDMA), polyethyleneglycol dimethacrylate, and mixtures thereof.

11. The curable dental composition of claim 1 wherein the inorganic oxide filler comprises nanoparticles.

12. The curable dental composition of claim 11 wherein the inorganic oxide nanoparticles comprise silica, zirconia, or mixtures thereof.

13. The curable dental composition of claim 11 wherein the inorganic oxide nanoparticles are in the form of nano-clusters.

14. The curable dental composition of claim 11 comprising a surface modified inorganic oxide filler.

15. A method of treating a tooth surface, the method comprising
  a) providing a curable dental resin of claim 1;
  b) placing the dental composition on a tooth surface in the mouth of a subject; and
  c) hardening the hardenable dental composition.

16. The method of claim 15 wherein the dental composition is a dental restoration composition.

17. A dental article comprising the curable dental composition of claim 1 at least partially cured.

18. A universal dental restorative comprising:
  a) 15-30 wt. % of a curable dental composition of claim 1;
  b) 70-85 wt. % of an inorganic filler;
  c) an initiator and
  <2%, stabilizers or pigments.

19. A flowable restorative composite comprising:
  a) 25-50 wt. % of a curable dental composition of claim 1;
  b) 30-75 wt. % of an inorganic filler;
  c) an initiator;
  d) <2% stabilizers and pigments; and
  e) optionally 5-60 wt. % monomers having an acid-functional group.

* * * * *